(12) United States Patent
Manabe

(10) Patent No.: US 9,533,956 B2
(45) Date of Patent: Jan. 3, 2017

(54) METHOD OF MANUFACTURING PYRIDAZINONE COMPOUND

(71) Applicant: SUMITOMO CHEMICAL COMPANY, LIMITED, Tokyo (JP)

(72) Inventor: Akio Manabe, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 14/779,383

(22) PCT Filed: Mar. 17, 2014

(86) PCT No.: PCT/JP2014/057953
§ 371 (c)(1),
(2) Date: Sep. 23, 2015

(87) PCT Pub. No.: WO2014/157021
PCT Pub. Date: Oct. 2, 2014

(65) Prior Publication Data
US 2016/0060225 A1    Mar. 3, 2016

(30) Foreign Application Priority Data
Mar. 26, 2013    (JP) .................. 2013-063493

(51) Int. Cl.
*C07D 211/70*    (2006.01)
*C07D 211/82*    (2006.01)
(Continued)

(52) U.S. Cl.
CPC ........... *C07D 237/14* (2013.01); *C07D 237/16* (2013.01); *C07D 307/60* (2013.01)

(58) Field of Classification Search
None
See application file for complete search history.

(56) References Cited

U.S. PATENT DOCUMENTS 5,691,374 A    11/1997    Black et al.
2008/0194566 A1    8/2008    Morishita et al.
(Continued)

FOREIGN PATENT DOCUMENTS

ES    454136 A1    12/1977
JP    11-505534 A    5/1999
(Continued)

OTHER PUBLICATIONS

International Search Report, issued in PCT/JP2014/057953, dated May 20, 2014.
(Continued)

*Primary Examiner* — Jeffrey H Murray
(74) *Attorney, Agent, or Firm* — Birch, Stewart, Kolasch & Birch, LLP

(57) ABSTRACT

A compound represented by formula (2)

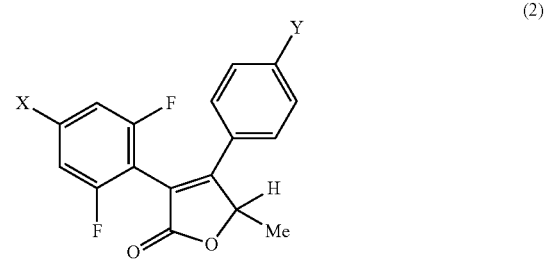

wherein X represents a hydrogen atom, a fluorine atom, a chlorine atom or a bromine atom, and Y represents a hydrogen atom, a fluorine atom, a chlorine atom or a bromine atom, is reacted with a brominating agent and an alkanol having 1 to 6 carbon atoms in the presence of a base to obtain a compound represented by formula (3)

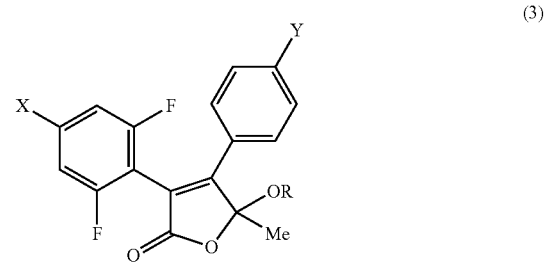

wherein R represents a C1 to C6 alkyl group, and X and Y represent the same meaning as described above, and then the compound represented by the formula (3) is reacted with hydrazine, whereby a compound represented by formula (1)

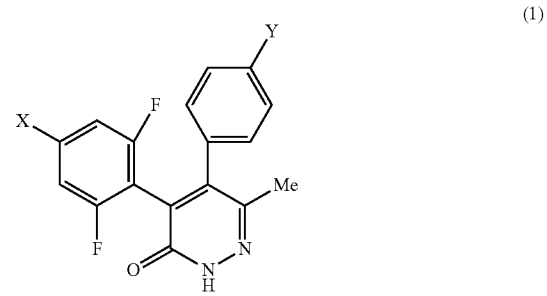

wherein X and Y represent the same meaning as described above, which is useful as a production intermediate of a fungicide, can be obtained.

12 Claims, No Drawings

(51) Int. Cl.
*C07D 237/00* (2006.01)
*C07D 237/02* (2006.01)
*C07D 237/14* (2006.01)
*C07D 237/16* (2006.01)
*C07D 307/60* (2006.01)

(56) References Cited

U.S. PATENT DOCUMENTS

| | | |
|---|---|---|
| 2013/0131067 A1 | 5/2013 | Matsuzaki |
| 2013/0137658 A1 | 5/2013 | Matsuzaki |
| 2013/0137683 A1 | 5/2013 | Matsuzaki |
| 2013/0137692 A1 | 5/2013 | Matsuzaki |
| 2015/0376138 A1 | 12/2015 | Nakae et al. |

FOREIGN PATENT DOCUMENTS

| | | |
|---|---|---|
| JP | 2006-22084 A | 1/2006 |
| WO | WO 2005/121104 A1 | 12/2005 |
| WO | WO 2010/036553 A1 | 4/2010 |
| WO | WO 2011/017261 A1 | 4/2010 |
| WO | WO 2012/020772 A1 | 2/2012 |
| WO | WO 2012/020774 A1 | 2/2012 |
| WO | WO 2012/020776 A1 | 2/2012 |
| WO | WO 2012/020778 A1 | 2/2012 |
| WO | WO 2014/129612 A1 | 8/2014 |
| WO | WO 2014/188863 A1 | 11/2014 |

OTHER PUBLICATIONS

Black et al., "3,4-Diaryl-5-hydroxyfuranones: Highly Selective Inhibitors of Cyclooxygenase-2 with Aqueous Solubility," Bioorganic & Medicinal Chemistry Letters, vol. 13, Mar. 1, 2003, pgs. 1195-1198.

Extended European Search Report dated Aug. 1, 2016, for European Application No. 14776160.5.

Lüthy et al., "7-(4,6-Dimethoxypyrimidinyl)oxy- and -thiophthalides as novel herbicides: Part 1. CGA 279 233: a new grass-killer for rice," Pest Management Science, vol. 57, Mar. 16, 2001, pgs. 205-224.

Chapleo et al., "Synthesis of Bromo-substituted 2-Buten- and 2-Penten-4-olides," Helvetica Chimica Acta, vol. 59, Issue 1, pp. 100-107 (9 pages), 1976 (Dec. 31, 1976).

De March et al., "Easy Access to 5-Alkyl-4-bromo-2(5H)-furanones: Synthesis of a Fimbrolide, an Acetoxyfimbrolide, and Bromobeckerelide," J. Org. Chem., vol. 60, No. 6, pp. 1814-1822 (10 pages), 1995 (Mar. 31, 1995).

METHOD OF MANUFACTURING PYRIDAZINONE COMPOUND

TECHNICAL FIELD

The present invention relates to a method for producing a pyridazinone compound and an intermediate thereof.

BACKGROUND ART

U.S. Pat. No. 7,569,518 describes that a compound represented by formula (1)

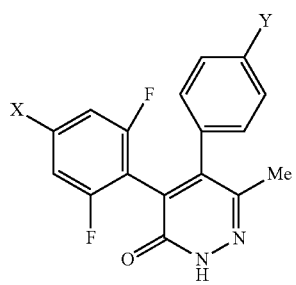

(1)

wherein X represents a hydrogen atom, a fluorine atom, a chlorine atom or a bromine atom, and Y represents a hydrogen atom, a fluorine atom, a chlorine atom or a bromine atom, and the like are useful as a production intermediate of a fungicide.

SUMMARY OF THE INVENTION

The present invention provides an effective method for producing a compound represented by the formula (1).

The present invention is as described below.

[1] A method for producing a compound represented by formula (1)

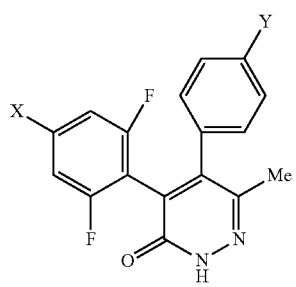

(1)

wherein X represents a hydrogen atom, a fluorine atom, a chlorine atom or a bromine atom, and Y represents a hydrogen atom, a fluorine atom, a chlorine atom or a bromine atom, (hereinafter, referred to as compound (1)), the method comprising:

reacting a compound represented by formula (2)

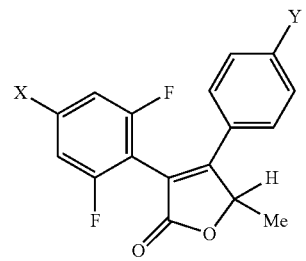

(2)

wherein X and Y represent the same meaning as described above, (hereinafter, referred to as compound (2)) with a brominating agent and a lower alkanol in the presence of a base; and reacting the reaction product with hydrazine.

[2] A method for producing a compound represented by formula (3)

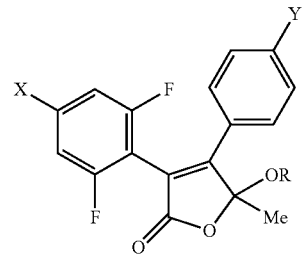

(3)

wherein R represents a C1 to C6 alkyl group, and X and Y represent the same meaning as described above, (hereinafter, referred to as compound (3)), the method comprising:

reacting a compound represented by formula (2)

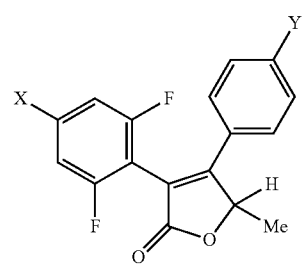

(2)

wherein X and Y represent the same meaning as described above, with a brominating agent and a lower alkanol in the presence of a base.

[3] A method for producing a compound represented by formula (1)

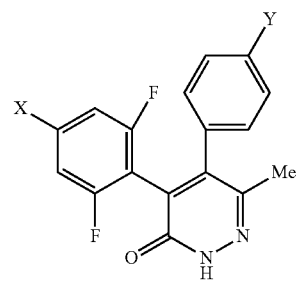

(1)

wherein X and Y represent the same meaning as described above,
the method comprising:
reacting a compound represented by formula (3)

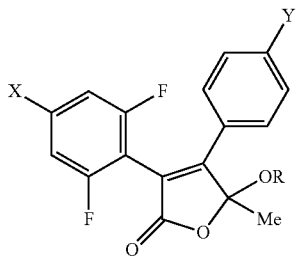

(3)

wherein R, X and Y represent the same meaning as described above,
with hydrazine.

[4] A compound represented by formula (3)

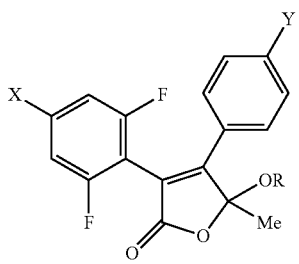

(3)

wherein R, X and Y represent the same meaning as described above.

MODE FOR CARRYING OUT THE INVENTION

The method of the present invention will be described in detail below.

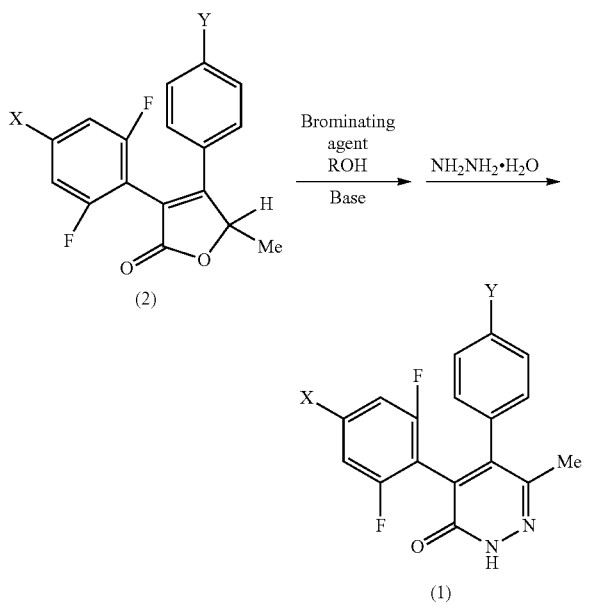

wherein R, X and Y represent the same meaning as described above.

The present invention comprises a step of reacting compound (2) with a brominating agent and a lower alkanol in the presence of a base (Step 1), and a step of reacting the reaction product obtained in Step 1 with hydrazine (Step 2).

Compound (3) that is the reaction product obtained in Step 1 may be isolated and then reacted with hydrazine to produce compound (1), and may be reacted with hydrazine to produce compound (1) without isolation.

First, Step 1 will be described.

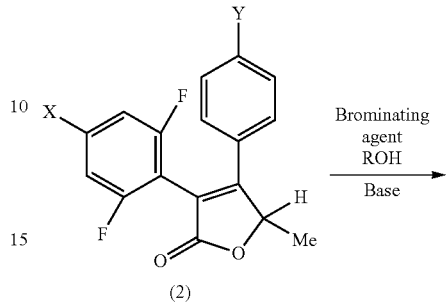

(2)

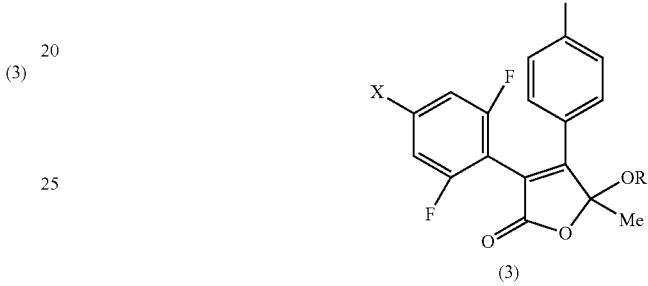

(3)

Step 1 is usually carried out in a solvent. Examples of the solvent include hydrocarbons such as toluene and xylene, halogenated hydrocarbons such as chlorobenzene and dichlorobenzene, and mixtures thereof.

In the present invention, the lower alkanol is an alkanol having 1 to 6 carbon atoms represented by formula

ROH wherein R represents the same meaning as described above, and a primary or secondary alkanol is usually used. Specific examples thereof are methanol, ethanol, propanol, butanol, pentanol, hexanol, 2-propanol, sec-butyl alcohol, pentan-2-ol and hexan-2-ol, and methanol is preferred.

The use amount of the lower alkanol is usually at a ratio of 2 to 3 mol, based on 1 mol of the compound (2). A lower alkanol such as methanol may be used as a solvent, and in that case, the amount of the lower alkanol is usually 2 to 200 mols per mol of the compound (2).

Examples of the brominating agent used in the present invention include bromine, N-bromosuccinimide, sodium bromoisocyanurate, dibromoisocyanuric acid, and 1,3-dibromo-5,5-dimethylhydantoin.

The use amount of the brominating agent is usually 0.5 to 3 mols, and preferably 1 to 1.2 mols, per mol of the compound (2).

Examples of the base include carbonates such as potassium carbonate and sodium carbonate, and the use amount thereof is usually 2 to 3 mols per mol of the compound (2).

The reaction temperature is usually within the range of −30 to 30° C., and the reaction time is usually within the range of 1 to 10 hours.

Step 1 is usually carried out by a method of preliminarily mixing the compound (2), a base and a lower alkanol, and then adding a brominating agent thereto.

After completion of the reaction, for example, the reaction mixture is mixed with water or ice water, and an organic layer obtained by extracting the mixture with an organic solvent is subjected to operations such as drying and concentration, whereby compound (3) can be isolated. The isolated compound (3) also can be further purified by chromatography, recrystallization, or the like.

Next, Step 2 will be described.

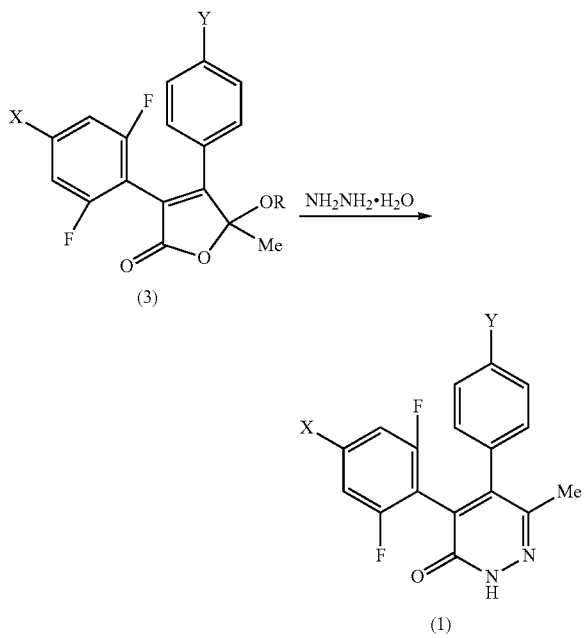

Step 2 is usually carried out in a solvent. Examples of the solvent include alcohols such as butanol, propanol, 2-propanol, ethanol and methanol, hydrocarbons such as toluene and xylene, halogenated hydrocarbons such as chlorobenzene and dichlorobenzene, water and mixtures thereof.

Hydrazine is usually used as a hydrate, and the amount thereof is usually 1 to 10 mols, and preferably 1 to 3 mols per mol of the compound (3).

The reaction temperature is usually within the range of 0 to 120° C., and the reaction time is usually within the range of 1 to 100 hours.

After completion of the reaction, for example, the reaction mixture is subjected to operations such as collecting the produced solid by filtration, whereby the compound (1) can be isolated. The isolated compound (1) also can be further purified by chromatography, recrystallization, or the like.

The compound (2) which is a raw material can be obtained, according to the following method.

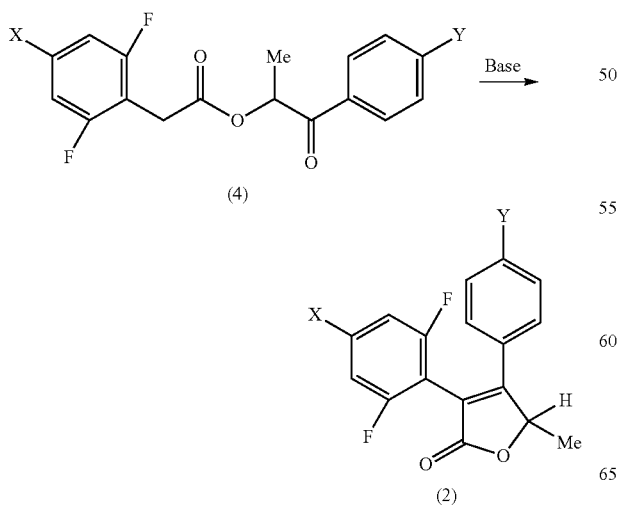

Namely, the compound (2) can be obtained by reacting a compound represented by formula (4) (hereinafter, referred to as compound (4)) with a base.

The reaction is usually carried out in a solvent. Examples of the solvent include nitriles such as acetonitrile, hydrocarbons such as toluene and xylene, halogenated hydrocarbons such as chlorobenzene and dichlorobenzene, and mixtures thereof.

Examples of the base include cyclic amines such as 1,8-diazabicyclo[5.4.0]undec-7-ene (hereinafter, referred to as DBU), tertiary amines such as triethylamine and diisopropylethylamine, and inorganic bases such as potassium carbonate and sodium carbonate, and the use amount thereof is usually at a ratio of 1 to 3 mol, and preferably 1 to 1.5 mol, based on 1 mol of the compound (4).

The reaction temperature depends on the kind of base to be used, and is usually within the range of −10 to 60° C., and the reaction time is usually within the range of 1 to 20 hours.

After completion of the reaction, for example, the reaction mixture is mixed with water or ice water, and an organic layer obtained by extracting the mixture with an organic solvent is subjected to operations such as drying and concentration, whereby the compound (2) can be isolated. The isolated compound (2) also can be further purified by chromatography, recrystallization, or the like.

The compound (4) can be obtained, according to the following method.

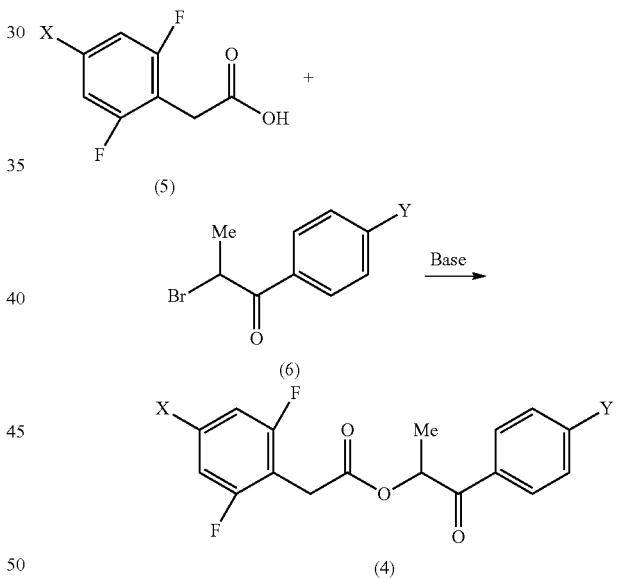

Namely, the compound (4) can be obtained by reacting a compound represented by formula (5) (hereinafter, referred to as compound (5)) with a compound represented by formula (6) (hereinafter, referred to as compound (6)) in the presence of a base.

The reaction is usually carried out in a solvent. Examples of the solvent include nitriles such as acetonitrile, hydrocarbons such as toluene and xylene, halogenated hydrocarbons such as chlorobenzene and dichlorobenzene, and mixtures thereof.

Examples of the base include tertiary amines such as triethylamine and diisopropylethylamine, and inorganic bases such as potassium carbonate, sodium carbonate, sodium hydroxide and potassium hydroxide, and the use amount thereof is usually 1 to 1.5 mols per mol of the compound (5).

The amount of the compound (6) used in the reaction is usually 0.8 to 1.1 mols pre mol of the compound (5).

The reaction temperature depends on the kind of base to be used, and is usually within the range of −10 to 30° C., and the reaction time is usually within the range of 1 to 20 hours.

After completion of the reaction, for example, the reaction mixture is mixed with water or ice water, and the mixture is extracted with an organic solvent, washed with sodium bicarbonate water or the like, if necessary, and then subjected to operations such as drying and concentration, whereby the compound (4) can be isolated. The isolated compound (4) also can be further purified by chromatography, recrystallization, or the like.

As the compound (5) and the compound (6), those commercially available can be used, and the compound also can be produced by a known method.

Examples of the embodiments of the compound (3) include the following compounds.

In the formula (3), compounds wherein R is a methyl group;

In the formula (3), compounds wherein X is a hydrogen atom;

In the formula (3), compounds wherein Y is a hydrogen atom;

In the formula (3), compounds wherein X and Y are a hydrogen atom;

In the formula (3), compounds wherein R is a methyl group, and X and Y are a hydrogen atom;

In the formula (3), compounds wherein X is a hydrogen atom, and Y is a chlorine atom;

In the formula (3), compounds wherein X is a fluorine atom, and Y is a hydrogen atom; and In the formula (3), compounds wherein X is a fluorine atom, and Y is a chlorine atom.

EXAMPLES

Hereinbelow, the present invention will be described in more detail by examples. However, the present invention is not limited to these examples.

Example 1

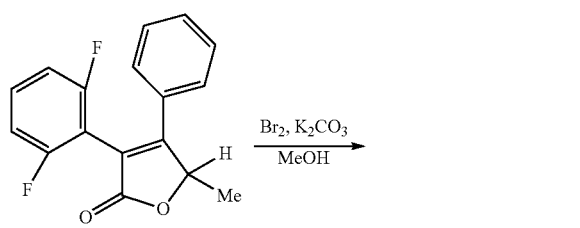

2.86 g of 3-(2,6-Difluorophenyl)-5-methyl-4-phenyl-2 (5H)-furanone was dissolved in 54 mL of methanol, and 2.76 g of potassium carbonate was added at −20° C. under a nitrogen atmosphere. Subsequently, a solution of 1.60 g of bromine dissolved in 10 ml of methanol was added dropwise thereto at −20° C. over 40 minutes, and stirred at the same temperature for 1 hour and then at 20° C. for 1 hour. The reaction liquid was filtered, and the filtrate was concentrated under reduced pressure. Water and tert-butyl methyl ether (hereinafter, referred to as MTBE) were added to the residue, and the mixture was separated. The organic layer was washed with water, dried over anhydrous sodium sulfate, and then concentrated under reduced pressure to give 3.04 g of residue. 1.52 g of the residue was subjected to a silica gel column chromatography (elution solvent: hexane-ethyl acetate) to obtain 1.30 g of 3-(2,6-difluorophenyl)-5-methoxy-5-methyl-4-phenyl-2(5H)-furanone (hereinafter, referred to as compound (i)). Yield: 82%

Compound (i)

$^1$H-NMR (CDCl$_3$, TMS) δ (ppm): 1.77 (3H, s), 3.42 (3H, s), 6.85-6.90 (1H, m), 7.05-7.10 (1H, m), 7.32-7.49 (6H, m)

Example 2

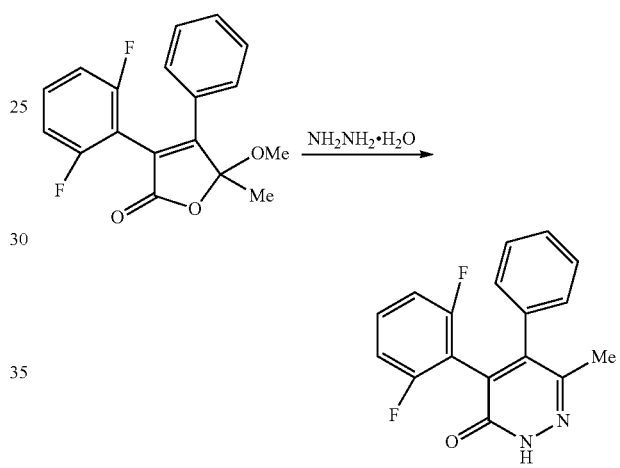

0.32 g of the compound (i) was suspended in 1.6 g of butanol, 0.06 g of hydrazine monohydrate was added thereto, and then the mixture was stirred under heat-refluxing for 5 hours. Thereafter, 0.06 g of hydrazine monohydrate and 1.6 g of butanol were added, and the mixture was stirred under heat-reflux for further 3 hours. After cooling, the precipitated solid was collected by filtration, and washed with a solution of a mixture of MTBE-hexane (1:1), to obtain 0.28 g of 4-(2,6-difluorophenyl)-6-methyl-5-phenyl-2H-pyridazin-3-one (hereinafter, referred to as compound (I)). Yield: 94%

Compound (I)

$^1$H-NMR (CDCl$_3$, TMS) δ (ppm): 2.14 (3H, s), 6.74-6.79 (2H, m), 7.09-7.31 (6H, m), 11.26 (1H, br s)

Example 3

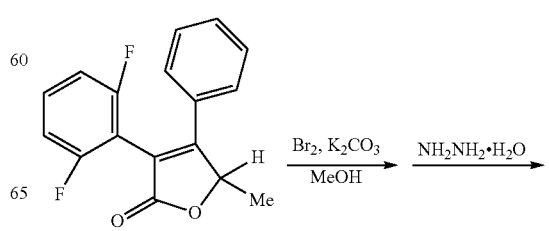

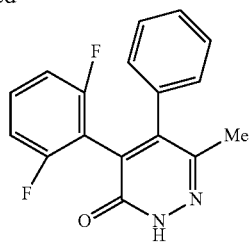

2.86 g of 3-(2,6-Difluorophenyl)-5-methyl-4-phenyl-2 (5H)-furanone was dissolved in 54 mL of methanol, and 2.76 g of potassium carbonate was added at −20° C. under a nitrogen atmosphere. Subsequently, a solution of 1.60 g of bromine dissolved in 10 ml of methanol was added dropwise thereto at −20° C. over 40 minutes, and stirred at the same temperature for 1 hour and then at 20° C. for 1 hour. The reaction liquid was filtered, and the filtrate was concentrated under reduced pressure. Water and MTBE were added to the residue, and the mixture was separated. The organic layer was washed with water, dried over anhydrous sodium sulfate, and then concentrated under reduced pressure give 3.04 g of residue. 1.52 g of the residue was suspended in 9 ml of butanol, 0.30 g of hydrazine monohydride was added thereto, and then the mixture was stirred under heat-refluxing for 5 hours. Thereafter, 0.30 g of hydrazine monohydride was added, and the mixture was stirred under heat-reflux for further 3 hours. After ice cooling for 1 hour, the precipitated solid was collected by filtration, and washed with a solution of a mixture of MTBE-hexane (1:1), to obtain 1.14 g of the compound (I). Yield: 76%

Reference Production Example 1

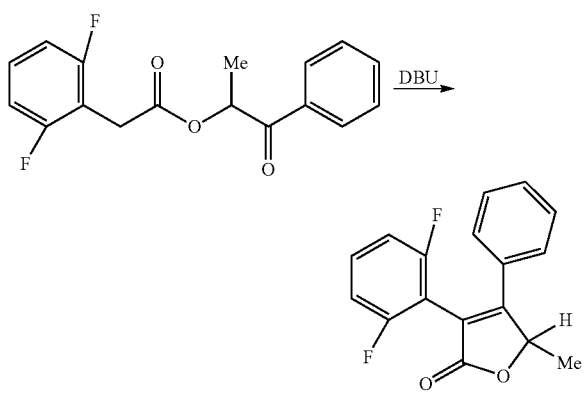

15.21 g of 1-(Benzoyl)ethyl 2,6-difluorophenylacetate was dissolved in 100 mL of acetonitrile, 7.61 g of DBU was added dropwise over 5 minutes while stirring under ice cooling, and then the mixture was stirred at 21° C. for 1 hour. 49 ml of 5% Hydrochloric acid was added dropwise to the reaction liquid under ice cooling, then water and MTBE were added, and the mixture was separated. The organic layer was washed with water and dried over anhydrous magnesium sulfate, and then concentrated under reduced pressure to obtain 14.06 g of 3-(2,6-difluorophenyl)-5-methyl-4-phenyl-2(5H)-furanone as a yellow solid.
$^1$H-NMR (CDCl3, TMS) δ (ppm): 1.54 (3H, d, J=6.8 Hz), 5.68 (1H, q, J=6.8 Hz) 6.82-6.86 (1H, m), 7.01-7.07 (1H, m), 7.22-7.47 (6H, m)

Reference Production Example 2

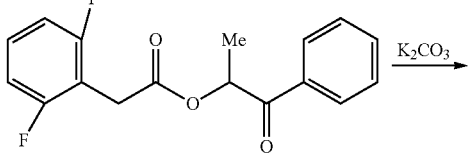

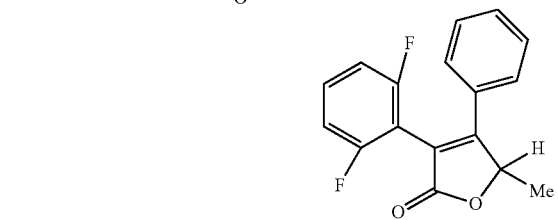

1.52 g of 1-(Benzoyl)ethyl 2,6-difluorophenylacetate was dissolved in 10 ml of acetonitrile, and 0.83 g of potassium carbonate was added while stirring. The mixture was stirred at 50 to 55° C. for 9 hours, and then 7.8 ml of 5% hydrochloric acid was added dropwise to the reaction liquid under ice cooling. Water and MTBE were added and the mixture was separated, then the organic layer was washed with water and dried over anhydrous magnesium sulfate, and then concentrated under reduced pressure. 1.46 g of the residue was subjected to a silica gel column chromatography (elution solvent: hexane-ethyl acetate) to obtain 1.10 g of 3-(2,6-difluorophenyl)-5-methyl-4-phenyl-2(5H)-furanone as a white solid.
$^1$H-NMR matched with the data in Reference Production Example 1.

Reference Production Example 3

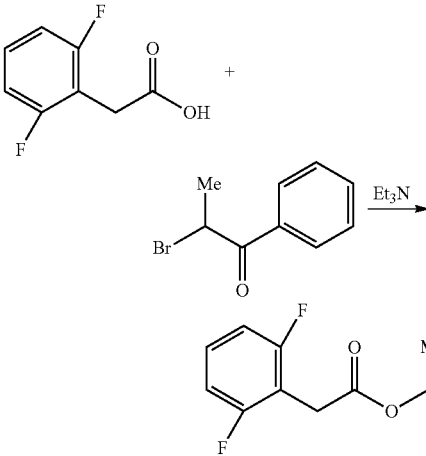

18.07 g of 2,6-Difluorophenyl acetic acid was dissolved in 40 ml of acetonitrile, and 21.31 g of α-bromopropiophenone and 40 ml of acetonitrile were added thereto. 13.15 g of Triethylamine was added dropwise while stirring under ice cooling, and the mixture was washed with 20 ml of acetonitrile. 0.86 g of 2,6-Difluorophenyl acetic acid and 1.01 g of triethylamine were added to the reaction liquid stirred at room temperature for 5 hours, and the mixture was further stirred at room temperature for 1 hour. About 70 g of acetonitrile was distilled off under reduced pressure, and water and ethyl acetate were added, and then separated. Separated organic phase was sequentially washed with sodium bicarbonate water and water, dried over anhydrous magnesium sulfate, and then concentrated under reduced pressure to obtain 28.37 g of 1-(benzoyl)ethyl 2,6-difluorophenylacetate as a light brown solid.

$^1$H-NMR (CDCl3, TMS) δ (ppm): 1.58 (3H, d, J=7.3 Hz), 3.82 (2H, s), 6.01 (1H, q, J=7.3 Hz) 6.85-6.91 (2H, m), 7.19-7.25 (1H, m), 7.43-7.59 (3H, m), 7.87-7.96 (2H, m)

INDUSTRIAL APPLICABILITY

According to the method of the present invention, a compound represented by formula (1) useful as the production intermediate of a fungicide can be produced.

The invention claimed is:

1. A method for producing a compound represented by formula (1)

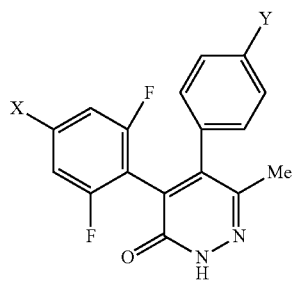

(1)

wherein X represents a hydrogen atom, a fluorine atom, a chlorine atom or a bromine atom, and Y represents a hydrogen atom, a fluorine atom, a chlorine atom or a bromine atom,
the method comprising:
reacting a compound represented by formula (2)

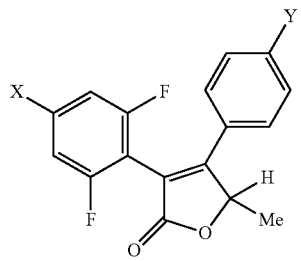

(2)

wherein X and Y represent the same meaning as described above,
with a brominating agent and an alkanol having 1 to 6 carbon atoms represented by formula

ROH wherein R represents a C1 to C6 alkyl group,
in the presence of a base; and
reacting the reaction product with hydrazine.

2. The method according to claim 1, wherein the brominating agent is bromine.

3. The method according to claim 1, wherein the brominating agent is bromine, and the alkanol is methanol.

4. The method according to claim 3, wherein the base is potassium carbonate or sodium carbonate.

5. A method for producing a compound represented by formula (1)

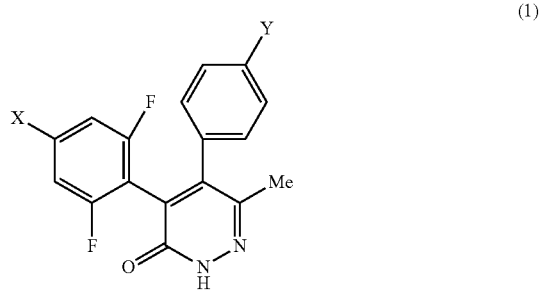

(1)

wherein X represents a hydrogen atom, a fluorine atom, a chlorine atom or a bromine atom, and Y represents a hydrogen atom, a fluorine atom, a chlorine atom or a bromine atom,
the method comprising:
reacting a compound represented by formula (3)

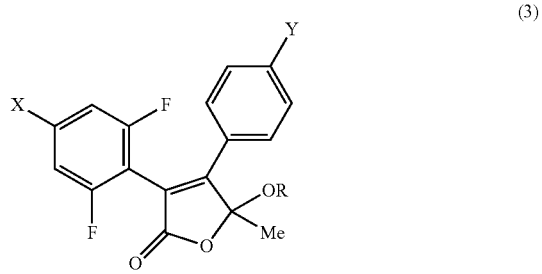

(3)

wherein R represents a C1 to C6 alkyl group, and X and Y represent the same meaning as described above,
with hydrazine.

6. A compound represented by formula (3)

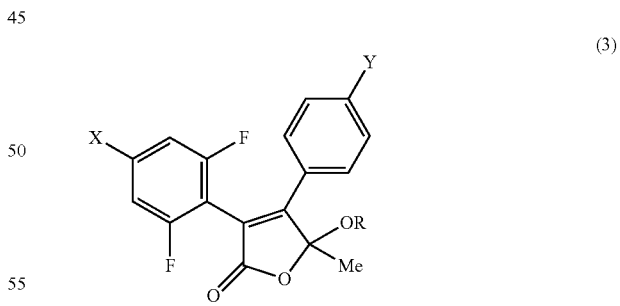

(3)

wherein R represents a C1 to C6 alkyl group, X represents a hydrogen atom, a fluorine atom, a chlorine atom or a bromine atom, and Y represents a hydrogen atom, a fluorine atom, a chlorine atom or a bromine atom.

7. The compound according to claim 6, wherein R is a methyl group.

8. The compound according to claim 6, wherein X is a hydrogen atom.

9. The compound according to claim 6, wherein Y is a hydrogen atom.

10. The compound according to claim 6, wherein X and Y are a hydrogen atom.

11. The compound according to claim 6, wherein R is a methyl group, and X and Y are a hydrogen atom.

12. A method for producing a compound represented by formula (3)

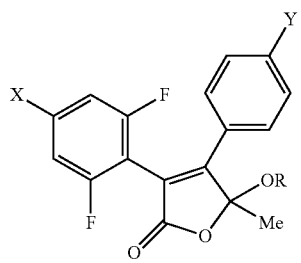
(3)

wherein R represents a C1 to C6 alkyl group, X represents a hydrogen atom, a fluorine atom, a chlorine atom or a bromine atom, and Y represents a hydrogen atom, a fluorine atom, a chlorine atom or a bromine atom, the method comprising:
reacting a compound represented by formula (2)

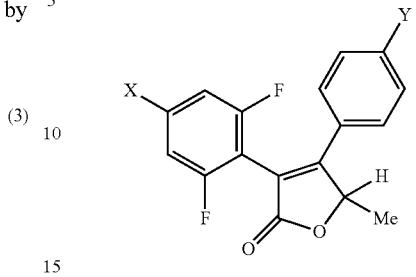
(2)

wherein X and Y represent the same meaning as described above,
with a brominating agent and an alkanol having 1 to 6 carbon atoms represented by formula
ROH wherein R represents the same meaning as described above, in the presence of a base.

* * * * *